United States Patent
Hausheer

(10) Patent No.: US 7,176,192 B2
(45) Date of Patent: Feb. 13, 2007

(54) METHOD FOR TREATING PATIENTS FOR RADIATION EXPOSURE

(75) Inventor: Frederick H. Hausheer, Boerne, TX (US)

(73) Assignee: BioNumerik Pharmaceuticals, Inc., San Antonio, TX (US)

( * ) Notice: Subject to any disclaimer, the term of this patent is extended or adjusted under 35 U.S.C. 154(b) by 0 days.

(21) Appl. No.: 10/002,526

(22) Filed: Oct. 26, 2001

(65) Prior Publication Data

US 2003/0092681 A1    May 15, 2003

(51) Int. Cl.
| | |
|---|---|
| *A61K 31/095* | (2006.01) |
| *A61K 31/105* | (2006.01) |
| *A61K 31/185* | (2006.01) |
| *A61K 31/255* | (2006.01) |
| *A61K 31/662* | (2006.01) |

(52) U.S. Cl. .................... 514/108; 514/109; 514/126; 514/127; 514/517; 514/578; 514/707

(58) Field of Classification Search ................ 514/108, 514/127, 274, 283
See application file for complete search history.

(56) References Cited

U.S. PATENT DOCUMENTS 5,770,576 A * 6/1998 Morozov et al. ............. 514/19
5,789,000 A   8/1998 Hausheer et al.

OTHER PUBLICATIONS

Plowman et al., Lancet, 1(8525), p. 167 (Jan. 17, 1987).*
van den Broeke et al., J. Photochem. Photobiol., 17(3), pp. 279-286 (1993).*
Facts & Comparisons, 48th edition (1994) p. 2841.*
Norbert Brock et al., "Studies on the Urotoxicity of Oxazaphosphorine Cytostatics and its Prevention. 2. Comparative Study on the Uroprotective Efficacy of Thiols and Other Sulfur Compounds," *Eur. J. Cancer Clin. Oncol.*, 17:1155-1163 (1981).
Theodore L. Phillips, MD., "Chemical Modification of Radiation Effects," *Cancer* 39:987-999 (1977).

* cited by examiner

*Primary Examiner*—Phyllis G. Spivack
(74) *Attorney, Agent, or Firm*—Akin Gump Strauss Hauer & Feld

(57) ABSTRACT

This invention relates to a method of treating a patient suffering from ionizing radiation exposure, or of treating a patient about to undergo ionizing radiation therapy. The method includes administering to a patient in need of treatment an effective amount of a thiol or reducible disulfide compound according to the formula set forth in the specification.

21 Claims, No Drawings

METHOD FOR TREATING PATIENTS FOR RADIATION EXPOSURE

FIELD OF THE INVENTION

This invention relates to a method for treating patients who have been exposed to ionizing radiation. The method involves administering an effective amount of a disulfide or thiol-containing compound to a patient who has been or will be exposed to external or internal sources of ionizing radiation.

BACKGROUND OF THE INVENTION

Exposure to ionizing radiation can occur in many ways, both accidental and therapeutic. The most familiar exposure to radiation occurs when cancer patients undergo radiation therapy as part of their treatment.

Organs and body systems most sensitive to the effects of ionizing radiation include the skin, hematopoietic and lymphatic systems, gonads, lungs, nerve tissues and the GI tract. In the case of whole body radiation exposure, all organ systems will be exposed to the effects of ionizing radiation.

Radiation cell damage is mediated by one or more mechanisms. In particular, cell damage is caused by the ionization of various cellular molecular systems (the "direct hit" theory for lipids in various membranes, breakage of the DNA strands, and other targets), or by the formation of free "hot" radicals (e.g., superoxide or hydroxyl radicals) in sufficient quantities to begin chain reactions to form other reactive free radicals, which react with, damage and eventually kill the affected cells (the "indirect hit" theory).

The most radiosensitive organs include the rapidly dividing cells of the intestine, kidneys and bone marrow. Conditions that may develop from exposure to radiation include xerostomia, esophagitis, colitis, proctitis, pneumonitis, dermatitis, nephritis, myelitis, pericarditis and myocarditis, and life threatening infections secondary to compromise of the normal bone marrow function and lowering of the blood neutrophil and lymphocyte counts, among others.

Radiation therapy for cancer is a widely used regimen of treatment for many common types of cancer, and is often employed in combination with surgery and/or chemotherapy. Despite modern safety precautions and improved methods of directing radiation at the tumor so as not to damage healthy cells, radiation therapy still presents significant risks to the patient.

Mesna (sodium 2-mercaptoethene sulfonate) and dimesna (disodium 2,2'-dithiobis ethane sulfonate) are known therapeutic compounds that have heretofore demonstrated a wide variety of therapeutic uses. Both mesna and dimesna have been shown to be effective protective agents against certain specific types of toxicity associated with the administration of cytotoxic drugs used to treat patients for various types of cancer.

In particular, mesna has been used with some success in preventing or mitigating the toxic effects of cytotoxic agents such as ifosfamide, oxazaphosphorine, melphalan, cyclophosphamide, trofosfamide, sulfosfamide, chlorambucil, busulfan, triethylene thiophosphamide, triaziquone, and others, as disclosed in U.S. Pat. No. 4,220,660, issued Sep. 2, 1980.

The near absence of toxicity of dimesna further underscores the usefulness of this compound, as large doses can be given to a patient without increasing the risk of adverse effects from the protective agent itself.

Further, pharmacological profiles of each compound indicate that, if proper conditions are maintained, mesna and dimesna do not prematurely inactivate primary therapeutic drugs to a significant degree. Thus, neither compound will significantly reduce activity of the chemotherapeutic agent, and in many cases, act to potentiate the effect of the main drug on targeted cancer cells.

The structures of both mesna and dimesna are shown below as Formula A and Formula B, respectively.

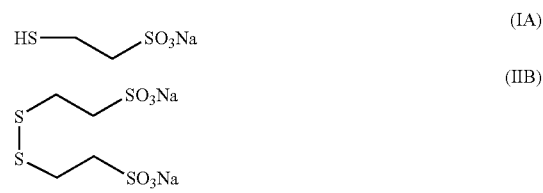

As is well known, dimesna is a dimer of mesna, with the optimum conditions for oxidation occurring in the slightly basic (pH~7.3), oxygen rich environment found in blood plasma. In mildly acidic, low oxygen conditions, in the presence of a reducing agent such as glutathione reductase, conditions prevalent in the kidneys, the primary constituent is mesna.

Mesna acts as a protective agent for a number of cytotoxic agents by substituting a nontoxic sulfhydryl moiety for a toxic TO hydroxy (or aquo) moiety. This action is particularly evidenced in the coadministration of mesna and oxazaphosphorine, and in the administration of dimesna along with cisplatin or carboplatin.

Mesna and dimesna, as well as some analogues of these compounds, have excellent toxicity profiles in mammalian species. However, it is clear from our earlier discoveries that dimesna has a much lower degree of toxicity relative to mesna; this lower degree of toxicity for dimesna imparts additional therapeutic value to this invention for radiation therapy since it is contemplated that chronic or high doses of dimesna will be needed in some circumstances in order to provide adequate prophylaxis for radiation toxicity as well as for treatment of acute or chronic radiation toxicity. In fact, dimesna has been administered intravenously to mice and dogs in doses higher than the accepted oral $LD_{50}$ for common table salt (3750 mg/kg), with no adverse effects. Dimesna has also been administered to humans in doses exceeding 15 $g/m^2$, with no major adverse effects.

Mesna, and other analogues with free thiol moieties, constitute the more physiologically active form of the two types of compounds described in this specification. These compounds manifest their activity by providing free thiol moieties for terminal substitution at locations where a terminal leaving group of appropriate configuration is located.

Dimesna and other disulfides can be activated intracellularly by glutathione reductase, a ubiquitous enzyme, thereby generating high concentrations of intracellular free thiols. These free thiols act to scavenge the radiation and other nucleophilic compounds often responsible for causing cell damage.

This profile is especially significant in explaining the success of dimesna in controlling and mitigating the toxic effects of platinum complex antitumor drugs. The mechanism for action in the case of cisplatin (cis-diammine dichloro platinum) is explained in U.S. Pat. No. 5,789,000, which is incorporated herein by reference.

Mesna, dimesna, and analogues of these compounds have been the subject of several prior pharmaceutical uses described in the literature and in prior patents, both in the United States and around the world. In addition to the cytotoxic agent protection uses, one or more of these compounds have proven effective, in vitro, against a multiplicity of biological targets, and have been effective, in vivo, in the treatment of sickle cell disease, chemical agent exposure, and other uses. Mesna, dimesna and analogues generally distribute well to the kidneys, intestine, bone marrow and extracellular space.

Mesna, dimesna, and analogues thereof are synthesized from commonly available starting materials, using acceptable routes well known in the art. One such method involves the two-step, single pot synthetic process for making dimesna and like compounds of the following formula:

$R_1$—S—$R_2$;

wherein:

$R_1$ is hydrogen, X-lower alkyl, or X-lower alkyl-$R_3$;

$R_2$ is -lower alkyl-$R_4$;

$R_3$ and $R_4$ are each individually $SO_3M$ or $PO_3M_2$;

X is absent or X is sulfur; and

M is an alkali metal.

The process essentially involves a two-step single pot synthetic process that results in the conversion of an alkenyl sulfonate salt or acid to the desired formula I compound. The process in the case of mesna is a single step process that converts the alkenyl sulfonate salt to mesna or a mesna derivative by reacting with an alkali metal sulfide or with hydrogen sulfide.

If the desired end product is dimesna or a dimesna analogue, a two-step single pot process is involved. Step 1 is as described above. Step 2 of the process is performed in the same reaction vessel as Step 1 without the need to purify or isolate the mesna formed during that step. Step 2 includes the introduction of oxygen gas into the vessel, along with an increase in pressure and temperature above ambient values, at least 20 pounds per square inch (psi) and at least 60° C. Dimesna or a derivative thereof is formed in essentially quantitative yield.

Other processes, well known and documented in the prior art, may be employed to make either mesna or dimesna, or derivatives and analogues thereof.

SUMMARY OF THE INVENTION

This invention involves the administration of an effective amount of a compound of formula I, below, for treating patients suffering from radiation sickness or for prophylactically treating a subject about to be exposed to ionizing radiation or about to undergo radiation therapy prior to beginning a radiation therapy session.

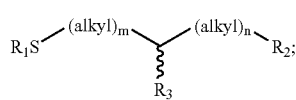
(I)

wherein:

$R_1$ is hydrogen, lower alkyl, a sulfur-containing amino acid or

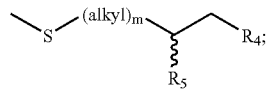

$R_2$ and $R_4$ are each individually $SO_3^-M^+$, $PO_3^{2-}M_2^{2+}$, or $PO_2S^{2-}M_2^{2+}$;

$R_3$ and $R_5$ are each individually hydrogen, hydroxy or sulfhydryl, where if $R_1$ is hydrogen, $R_3$ is not sulfhydryl;

m and n are individually 0, 1, 2, 3 or 4, with the proviso that if m or n is 0, then $R_3$ is hydrogen; and M is hydrogen or an alkali metal ion; or a pharmaceutically acceptable salt thereof.

Given the formula I structure, compounds that are contemplated to be effective in the treatment method of this invention include mesna, dimesna, the phosphonate salts of mesna or dimesna, certain hydroxylated derivatives thereof, and disulfide heteroconjugates of sulfur-containing amino acids, such as cysteine, homocysteine, glutathione and others.

Effective amounts of the formula I compounds to be administered according to the method of this invention vary, and depend on the severity of the patient's or subject's exposure to radiation, the route of administration, and other factors. Ranges of preferred dosage amounts and schedules, as well as preferred methods of administration are set forth below.

Accordingly, it is an object of this invention to provide for a method of safely and effectively treating a patient or subject for exposure to radiation or for prophylactically treating a subject about to be exposed to ionizing radiation or about to undergo radiation therapy.

Other objects will become apparent upon a reading of the following description.

DESCRIPTION OF THE PREFERRED EMBODIMENTS

The preferred embodiments herein described are not intended to be exhaustive or to limit the invention to the precise form disclosed. They are chosen and described to explain the principles of the invention, and its application and practical use to best enable others skilled in the art to follow its teachings.

The method of this invention involves the administration of an effective amount of a formula I compound to a patient who has been exposed to ionizing radiation from external sources or by ingestion of contaminated material. Alternatively, the method of this invention involves administering a formula I compound as a prophylactic treatment to a subject or a patient prior to the expected or possible exposure to ionizing radiation or to the patient receiving radiation therapy. Administration of the compounds may be either oral or parenteral.

In the case of unintentional exposure, the effective amount of the formula I compound will necessarily depend upon the timing, duration and severity of the patient's exposure, normally referred to as the cumulative dose in rads. Any dose greater than 50 rads is capable of producing adverse effects in a human, while doses of greater than 200 rads of total body radiation are potentially fatal. Since the formula I compounds are essentially nontoxic, large amounts can be safely administered to combat the effects of the radiation absorption.

The preferred dosage to treat radiation exposure may be as low as 0.1 mg/kg up to 1,000 mg/kg. The more severe or greater duration of the exposure, the greater the dosage and duration of treatment with formula I compound will be needed in order to provide an effective response. Repeated doses of the formula I compound are preferably administered to maintain effective plasma and tissue levels of formula I compound and/or its active metabolites in order to obtain maximum protective and therapeutic potential benefits of the agent.

Administration of formula I compound is preferably through parenteral or oral routes. For parenteral administration, the formula I compound is dissolved in a suitable solvent, most preferably sterile water for injection, to produce a sterile pyrogen free solution that may be injected or infused into a patient with safety. One or more pharmaceutically acceptable excipients may also be added to provide for an elegant formulation.

For oral administration the formula I compound is preferably combined with one or more pharmaceutically acceptable excipients, fillers and/or diluents. Oral dosage forms include pills, caplets, capsules, tablets, and others. The formula I compound may be contained in a swallowable container such as a gelatin capsule or the like. Alternatively, the formula I compound may be supplied as a wettable powder for mixing into solution or suspension, or may exist as a concentrated liquid solution, suspension or colloid.

Administration of the formula I compound should be prescribed as soon as possible after determining the patient's exposure to ionizing radiation. The preferred initial dose is between 20 mg/kg and 1,000 mg/kg, with succeeding doses dependent upon the condition and progress of the patient.

Other accepted methods may also be combined with the administration of the formula I compound. Due to the excellent safety profile and the rapid clearance rate, additional doses of the formula I compound may be administered safely.

When the formula I compounds are used as prophylaxis, the preferred initial dose is between 500 mg/m$^2$–40 g/m$^2$. Preferably the dose is administered 15 minutes to 1 hour prior to the onset of radiation therapy. The preferred route of administration is by intravenous infusion, or by oral solution, suspension, colloid or capsules or tablets. Administration of the formula I compound may also be repeated at regular intervals, preferably about every 4 hours beginning at 2 hours post treatment, as additional prophylaxis against undesired effects. Also the administration may be carried out by continuous infusion for more than one month with daily doses of 500 mg/m$^2$ to up to 120 grams/m$^2$ per day.

Currently, the most preferred regimen of treatment according to the invention is to administer to the patient or subject about 10 to 40 g/m$^2$ of disodium 2,2'-dithiobis ethane sulfonate by IV infusion, beginning the infusion at approximately 30–45 minutes prior to the start of the radiation therapy session. Oral doses of 10 to 80 g/m$^2$ of disodium 2.2'-dithiobis ethane sulfonate are administered at 2 hours post-treatment and at 6 hours post-treatment, with additional doses at 10 hours, et seq., determined by the patient's or subject's condition at that time.

It is understood that the above description is in no way limiting of the invention, which may be modified within the scope of the following claims.

What is claimed is:

1. A method of treating a human subject for exposure to ionizing radiation, said method comprising administering to the subject following the subject's exposure to the ionizing radiation an effective amount of a compound of formula I:

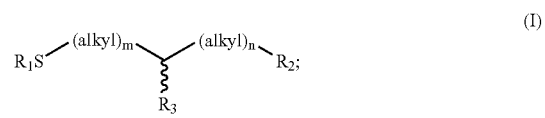

wherein:

R$_1$ is hydrogen, lower alkyl, a sulfur-containing amino acid or

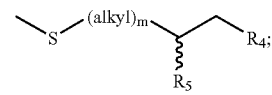

R$_2$ and R$_4$ are each individually SO$_3^-$M$^+$, PO$_3^{2-}$M$_2^{2+}$, or PO$_2$S$^{2-}$M$_2^{2+}$;

R$_3$ and R$_5$ are each individually hydrogen, hydroxy or suithydryl, where if R$_1$ is hydrogen, R$_3$ is not sulfhydryl;

m and n are individually 0, 1, 2, 3 or 4, with the proviso that if m or n is 0, then R$_3$ is hydrogen; and M is hydrogen or an alkali metal ion; or a pharmaceutically acceptable salt thereof.

2. The method of claim 1 wherein the formula I compound is 2,2'-dithiobis ethane sulfonic acid, or a disodium salt thereof, and the effective amount administered is from 0.1 mg/kg of body weight to 1,000 mg/kg of body weight of the subject.

3. The method of claim 1 wherein the compound is administered orally.

4. The method of claim 1 wherein the compound is administered parenterally.

5. The method of claim 1 wherein R$_1$ is lower alkyl, a sulfur-containing amino acid or

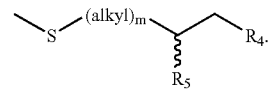

6. The method of claim 2 wherein the effective amount administered is from 20 mg/kg of body weight to 1,000 mg/kg of body weight of the subject.

7. A method of treating a human subject about to undergo exposure to ionizing radiation, said method comprising administering intravenously or orally to the subject prior to being exposed to the ionizing radiation, a compound of formula I, other than mesna, in an amount and at a time effective to prophylactically protect the subject from adverse effects of the ionizing radiation:

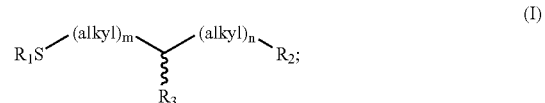

wherein:

R$_1$ is hydrogen, lower alkyl, a sulfur-containing amino acid or

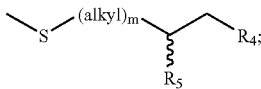

$R_2$ and $R_4$ are each individually $SO_3^-M^+$, $PO_3^{2-}M_2^{2+}$, or $PO_2S^{2-}M_2^{2+}$;

$R_3$ and $R^5$ are each individually hydrogen, hydroxy or sulfhydryl, where if $R_1$ is hydrogen, $R_3$ is not sulfhydryl;

m and n are individually 0, 1, 2, 3 or 4, with the proviso that if m or n is 0, then $R_3$ is hydrogen; and M is hydrogen or an alkali metal ion; or a pharmaceutically acceptable salt thereof.

8. The method of claim 7 wherein the effective amount of the formula I compound to be administered is 500 mg/m² to 40 g/m² of body surface area of the subject.

9. The method of claim 7 wherein $R_1$ is lower alkyl, a sulfur-containing amino acid or

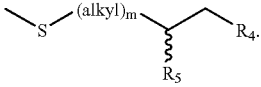

10. The method of claim 9 wherein the formula I compound to be administered is 2,2'-dithiobis ethane sulfonic acid, or a disodium salt thereof.

11. The method of claim 7 wherein administration is by intravenous infusion.

12. The method of claim 7 wherein administration is oral.

13. A method of treating a human subject about to undergo exposure to ionizing radiation, the method comprising administering intravenously or orally to the subject 15 minutes to 1 hour prior to being exposed to the ionizing radiation, an amount of a compound of formula I effective to prophylactically protect the subject from adverse effects of the ionizing radiation:

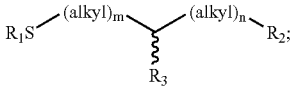 (I)

wherein:

$R_1$ is hydrogen, lower alkyl, a sulfur-containing amino acid or

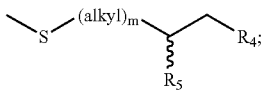

$R_2$ and $R_4$ are each individually $SO_3^-M^+$, $PO_3^{2-}M_2^{2+}$, or $PO_2S^{2-}M_2^{2+}$;

$R_3$ and $R_5$ are each individually hydrogen, hydroxy or sulfhydryl, where if $R_1$ is hydrogen, $R^3$ is not sulfhydryl;

m and n are individually 0, 1, 2, 3 or 4, with the proviso that if m or n is 0, then $R_3$ is hydrogen; and M is hydrogen or an alkali metal ion; or a pharmaceutically acceptable salt thereof, and wherein an additional effective dose of the formula I compound is administered about 2 hours after conclusion of the radiation exposure.

14. The method of claim 13 wherein additional effective doses are administered to the patient about every 4 hours after the first-mentioned additional effective dose.

15. The method of claim 13 wherein the additional effective dose is administered orally.

16. The method of claim 13 wherein the additional effective dose is administered by intravenous infusion.

17. A method of protecting a human subject against ionizing radiation, the method comprising administering to the subject an amount effective to protect the subject from adverse effects of the ionizing radiation of a compound of formula I, other than mesna:

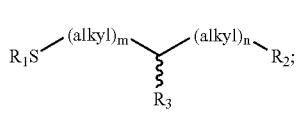 (I)

wherein:

$R_1$ is hydrogen, lower alkyl, a sulfur-containing amino acid or

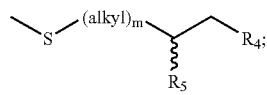

$R_2$ and $R_4$ are each individually $SO_3^-M^+$, $PO_3^{2-}M_2^{2+}$, or $PO_2S^{2-}M_2^{2+}$;

$R_3$ and $R_5$ are each individually hydrogen, hydroxy or sulfhydryl, where if $R_1$ is hydrogen, $R_3$ is not sulfhydryl;

m and n are individually 0, 1, 2, 3 or 4, with the proviso that if m or n is 0, then $R_3$ is hydrogen; and M is hydrogen or an alkali metal ion; or a pharmaceutically acceptable salt thereof.

18. The method of claim 17, wherein the compound is 2,2'-dithiobis ethane sulfonic acid, or a disodium salt thereof.

19. The method of claim 17 wherein administration is by intravenous infusion.

20. The method of claim 17 wherein administration is oral.

21. The method of claim 17 wherein $R_1$ is lower alkyl, a sulfur-containing amino acid, or

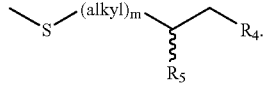

* * * * *